US00PP35177P2

(12) United States Plant Patent
Barritt et al.

(10) Patent No.: US PP35,177 P2
(45) Date of Patent: May 23, 2023

(54) APPLE TREE VARIETY NAMED 'WA 64'

(50) Latin Name: *Malus domestica*
Varietal Denomination: WA 64

(71) Applicant: Washington State University, Pullman, WA (US)

(72) Inventors: Bruce Barritt, Kelowna (CA); Katherine M. Evans, Wenatchee, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 0 days.

(21) Appl. No.: 17/803,723

(22) Filed: Oct. 26, 2022

(51) Int. Cl.
*A01H 6/74* (2018.01)
*A01H 5/08* (2018.01)

(52) U.S. Cl.
USPC ..... Plt./161
CPC ..... *A01H 6/7418* (2018.05)

(58) Field of Classification Search
USPC ..... Plt./161
See application file for complete search history.

*Primary Examiner* — Annette H Para
(74) *Attorney, Agent, or Firm* — Barnes & Thornburg LLP

(57) ABSTRACT

A new and distinct variety of '*Malus domestica*' apple tree named 'WA 64' and produced from a controlled cross of 'Honeycrisp' and 'Cripps Pink' is described herein. 'WA 64' is distinctly different from each of its parents and other mid-season apples.

5 Drawing Sheets

Latin name: '*Malus domestica*'.
Denominaiton: 'WA 64'.

BACKGROUND OF THE INVENTION

This invention refers to a new and distinct variety of apple tree '*Malus domestica*' which is named 'WA 64' and produced from a controlled cross of 'Honeycrisp' (U.S. Plant Pat. No. 7,197) and 'Cripps Pink' (U.S. Plant Pat. No. 7,880) that is distinctly different from each of its parents and other mid-season apples. 'WA 64' originated as a single seedling from a cross of the patented varieties 'Honeycrisp' and 'Cripps Pink' in 1998. Seeds were collected and seedlings established in a greenhouse in Wenatchee, Wash. in 1999. 'WA 64' was budded onto M9-337 rootstock in 2001 and established at the Washington State University Tree Fruit Research and Extension Center orchard block at Wenatchee, Wash. Following selection in 2006, second generation trees were budded to M9 rootstock in 2007 and planted in 2009 at Washington State University Sunrise Orchard, 75 Sunrise Court Rd, East Wenatchee, Douglas County, Wash.; USDA Hardiness zone 7a. A comparison of second generation 'WA 64' trees against the originally budded tree showed them to be essentially the same and stable over the years checked.

SUMMARY OF THE INVENTION

'WA 64' is an apple unlike either of its parents in that its mid-season maturity is nearly a month after that of 'Honeycrisp' and some six weeks before 'Cripps Pink'. Its apples are similar in shape to that of 'Honeycrisp' but slightly smaller and exhibit a higher percentage of surface coloring. The flesh of 'WA 64' resists browning following cutting to a much greater extent than either of its parents, is considerably firmer than 'Honeycrisp' at harvest, but similar/slightly less than that of 'Cripps Pink'. Harvest Maturity Brix Level of 'WA 64' is greater than that seen from 'Honeycrisp' but less than that of 'Cripps Pink' and acid levels are higher than that of 'Honeycrisp' but lower than that found with 'Cripps Pink'. 'WA 64' does not exhibit bitter-pit fruit disorder as frequently exhibited in 'Honeycrisp' fruit. Similar to both parents ('Honeycrisp' and 'Cripps Pink'), 'WA 64' is heterozygous for the ACS1 gene and homozygous (2,2) for the ACO1 gene, both of which are involved in ethylene production, which in turn affects storage life.

DETAILED DESCRIPTION OF THE INVENTION

Figure 1:
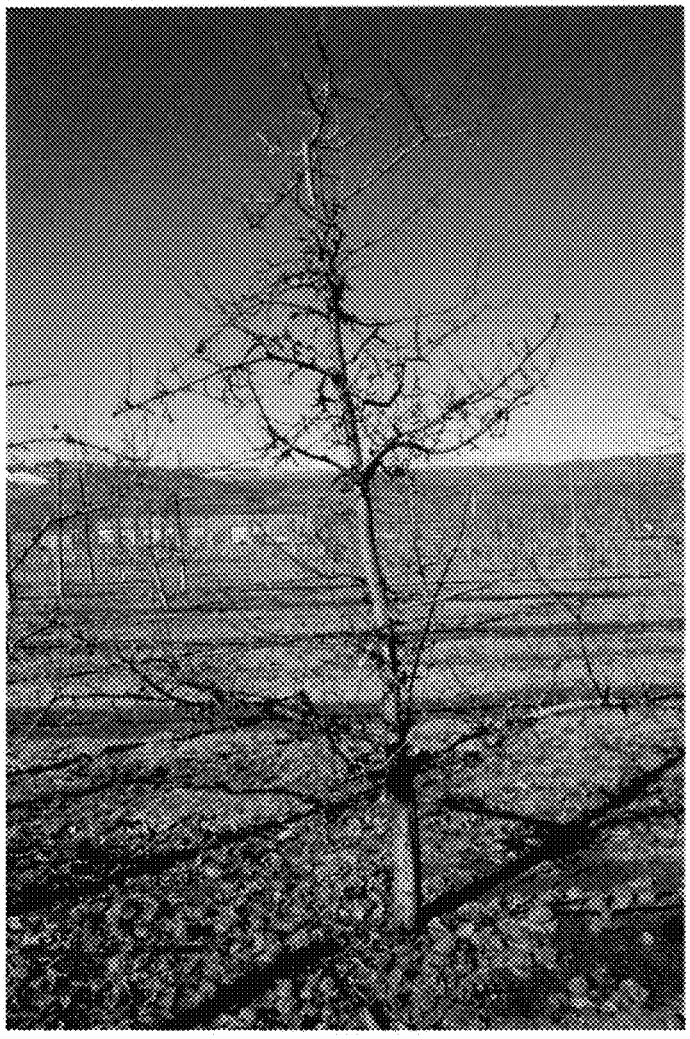
FIG. 1 is a view of 'WA 64' 10-year-old 2nd generation tree at full dormancy.
Figure 2:
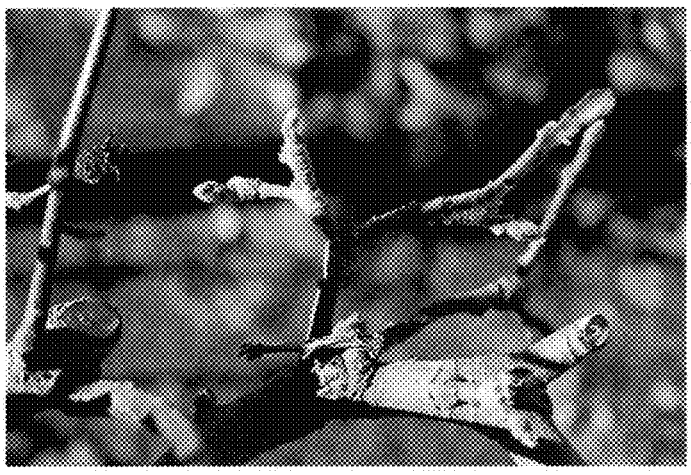
FIG. 2 is a view of typical 'WA 64' 10-year-old 2nd generation tree's spur development.
Figure 3:
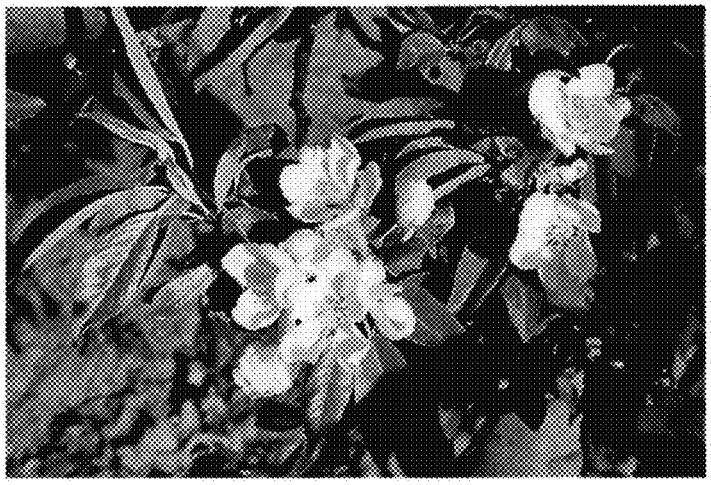
FIG. 3 is a view of 'WA 64' 10-year-old 2nd generation tree at blossoms at 90% full bloom.
Figure 4:
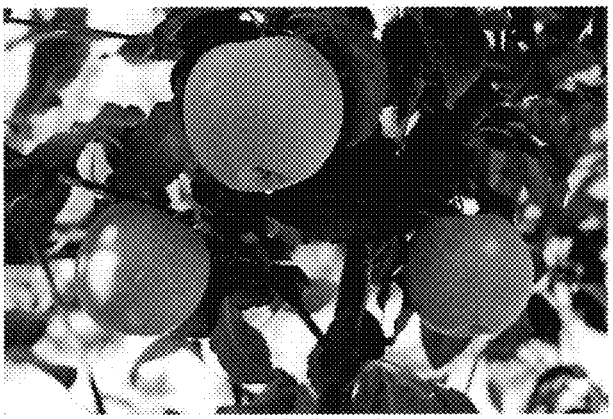
FIG. 4 is a view of fruiting limb of 'WA 64' 10-year-old 2nd generation tree at pre-harvest maturity.
Figure 5:
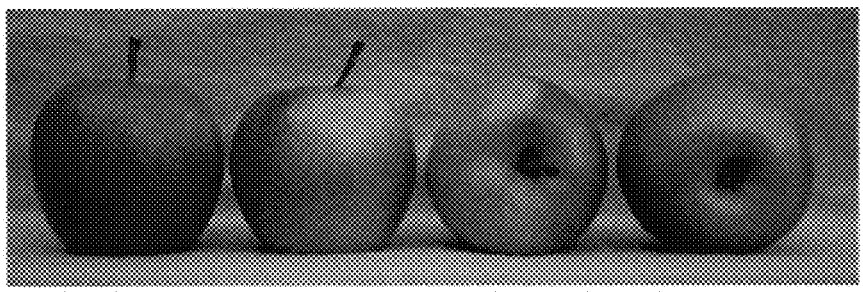
FIG. 5 shows various harvest mature positions of 2nd generation 'WA 64' fruit.

The following observations relate to a 'WA 64' 10-year-old 2nd generation tree. All color references are from The R.H.S. Colour Chart (2001 edition) provided by The Royal Horticultural Society of Great Britain. Common color names are also occasionally used.

Tree: As trained.

*Type*.—Tip bearer and semi-spur.
*Vigor*.—Considered moderate.
*Overall shape*.—As trained — cone shaped.
*Height*.—14'.
*Width*.—10'.

*Hardiness*.—Considered hardy where grown in central Washington State.

*Productivity*.—Considered high.

Trunk: 10.5 cm in diameter at 30 cm above ground.

*Bark texture*.—Mostly smooth with some cracking. Color: From the Grey-brown group 199A.

*Lenticels*.—15 lentils in a nine square centimeter area. Shape: Flat. Length: Ranges from 3.4 mm to 10.8 mm with an average of 7.1 mm. Width: Ranges from 1.1 mm to 1.5 mm. Color: From the Brown group N200A.

Branches: Scaffold branches.

*Bark texture*.—Smooth.

*Size*.—Diameter at 10 cm from trunk: Ranges from 29.7 mm to 37.0 mm with an average of 32.8 mm.

*Angle*.—As trained — 80 to 85 degrees.

*Bark color*.—From the Grey-brown group 199A.

*Lenticels*.—10 lentils in a nine square centimeter area. Shape: Flat. Length: Ranges from 2.7 mm to 5.2 mm with an average of 4.0 mm. Width: Ranges from 1.1 mm to 1.4 mm. Color: From the Greyed-orange group 163C.

Branches: $2^{nd}$ year fruiting branches.

*Bark texture*.—Smooth.

*Diameter at mid point*.—Ranges from 4.6 mm to 7.4 mm with an average of 5.6 mm.

*Bark color*.—From the Grey-brown group 199A.

*Pubescence*.—None.

*Lenticels*.—20 lentils in 1 cm section of branch. Shape: Mostly round, a few flat. Size: Diameter ranges from 0.8 mm to 1.3 mm; Length ranges from 1.9 mm to 2.4 mm; Width ranges from 0.6 mm to 1.1 mm. Color: Color from the White group 155C.

*Spur development*.—Spur Length: Ranges from 3.9 mm to 15.7 mm with an average of 8.2 mm. Bud Shape: Acute. Bud Length: Ranges from 6.2 mm to 8.9 mm with an average of 7.8 mm. Bud Diameter: Ranges from 3.5 mm to 5.0 mm with an average of 4.4 mm. Scale Color: From the greyed-purple group 187B. Pubescence: Lite to moderate in density covering 60% of surface. Color: Color is from the white group N155A.

Branches: Current Year branches.

*Texture*.—Bark is smooth.

*Size*.—Length: Ranges from 23 cm to 41 cm with an average of 33.4 cm. Diameter at midpoint: Ranges from 3.7 mm to 5.4 mm with an average of 4.4 mm. Pubescence: Moderate in density over 90% of surface area. Color: From the White group N155A.

*Bark color*.—From the greyed-brown group 199A.

*Lenticels*.—12 lenticels in 1 cm section of branch. Shape: Both round and flat. Diameter: Ranges from 0.2 mm to 0.6 mm. Length: Ranges from 1.1 mm to 1.9 mm. Width: Ranges from 0.3 mm to 0.4 mm. Color: From the greyed-yellow group 161A.

*Internode length*.—Ranges from 18.2 mm to 35.1 mm with an average of 27.2 mm.

Bloom:

*Full bloom date*.—Apr. 25, 2018.

*Number blossoms per bud*.—Ranges from 2 to 6, mostly 5.

*Size*.—Considered large. Diameter when fully open: ranges from 45 mm to 55 mm with an average of 49 mm. Petals: 5. Shape: Considered round oblong. Width: Ranges from 14.4 mm to 18.9 mm with an average of 16.6 mm. Length: Ranges from 19.3 mm to 22.2 mm with an average of 21.2 mm. Color: From the White group 155C. Undersurface highlights (0 to 50% surface area) from the Greyed-purple group 185C. Stamen: Number: Ranges from 16 to 21, mostly 20. Filament: Length: Ranges from 4.1 mm to 8.7 mm with an average of 6.7 mm. Color: From the White group 155A. Anthers: Shape: Kidney. Width: Ranges from 1.5 mm to 1.9 mm with an average of 1.7 mm. Length: Ranges from 1.8 mm to 2.4 mm with an average of 2.1 mm. Color: From the Yellow-white group 158A. Pollen: Moderate in abundance. Color: From the Greyed-Orange group 164A. Pistil: Style: Length: Ranges from 10.9 mm to 12.2 mm with an average of 11.4 mm. Splits into five branches at an average of 3.4 mm from base. Color: From the Yellow-Green group 145A. Pubescence: None. Stigma: Number: 5 Shape: Club. Color: From the Yellow-green group 145A. Sepal: Number: 5. Shape: Lanceolate. Tip: Acuminate. Base: Truncate. Length: Ranges from 9.7 mm to 13.8 mm with an average of 11.6 mm. Width: Ranges from 2.1 mm to 4.2 mm with an average of 3.7 mm. Color: From the Yellow-Green group 144B. Tips highlighted from the Greyed-Orange group 176A. Pubescence: Moderately heavy over 100% of surfaces. Color from the White group 155C. Peduncle: Length: Ranges from 24.2 mm to 31.6 mm with an average of 28.1 mm. Diameter at midpoint: Ranges from 1.0 mm to 1.2 mm with an average of 1.1 mm. Color: From the Yellow-Green group 144A. Pubescence: Moderate in density over 100% surface area. Color: From the White group 155C. Thalmus: Depth: Ranges from 3.4 mm to 5.4 mm with an average of 4.3 mm. Color: From the Greyed-orange group 176A. Pubescence: Abundant over 100% of surface area. Color from the White group 155C.

Leaves:

*Shape*.—Acute.

*Texture*.—Upper: Leathery and smooth. Lower: Smooth with raised veins.

*Sheen*.—Upper: High. Lower: Dull.

*Pubescence*.—Light density on 100% of lower surface only. Color: From the White group 155C.

*Length*.—Ranges from 6.9 cm to 8.8 cm with an average of 8.0 cm.

*Width*.—Ranges from 4.5 cm to 6.0 cm with an average of 5.2 cm.

*Margin*.—Serrate.

*Tip*.—Mostly acute, some acuminate.

*Base*.—Rounded.

*Blade color*.—Upper: From the Yellow-green Group 147A. Lower: From the Yellow-green Group 147B.

*Stipules*.—Present only on 10% of leaves and only as singles. Shape: Linear. Length: 4.1 mm. Width: 0.9 mm. Color: From the Yellow-green group 152B. Pubescence: None.

*Mid vein*.—Width at midpoint: Ranges from 1.1 mm to 1.6 mm with an average of 1.3 mm. Color: From the Yellow-green group 145C. Pubescence: Light density covering 100% of prominent undersurface. Color: From the White group 155B.

*Petiole*.—Has an indistinct groove running the entire length of the upper surface that appears flat. Length: Ranges from 3.1 cm to 4.6 cm with an average of 3.4 cm. Diameter at midpoint: Ranges from 1.2 mm to 1.6 mm with an average of 1.5 mm. Color: From the Yellow-green group 152B with the basal end highlighted from the Orange-red group N34A. Pubescence: light in density over entire surface. Color: From the White group 155C.

*Blade attitude*.—Slight drupe and mostly flat.

Fruit:

*Form*.—Mostly round with some slightly round-conical.

*Size*.—Equatorial Diameter: Ranges from 6.7 cm to 7.4 cm with an average of 7.1 cm. Axis Diameter: Ranges from 5.9 cm to 6.8 cm with an average of 6.3 cm.

*Stem*.—Is not clubbed. Length: Ranges from 2.2 cm to 3.1 cm with an average of 2.8 cm. Diameter: Ranges from 2.1 mm to 2.8 mm with an average of 2.4 mm. Color: From the Greyed-orange group 165A. Pubescence: Light density on the basal half. Color: From the Orange-white group 159D.

*Stem cavity*.—Lipped: No. Shape: Acute cone. Russet: No. Width: Ranges from 24.9 mm to 31.4 mm with an average of 26.9 mm. Depth: Ranges from 11.7 mm to 15.6 mm with an average of 13.2 mm.

*Basin cavity*.—Ribbed: No. Sides: Sloping and smooth. Width: Ranges from 22.4 mm to 26.7 mm with an average 25.1 mm. Depth: Ranges from 7.7 mm to 12.1 mm with an average of 9.2 mm. Eye: Erect convergent with occasional reflexed tips. Pubescence: Moderate in density. Color: From the White group 155C.

*Skin*.—Smooth. Appearance: A light stripe. Color: Stripe from the Red group 47B. Background from the Yellow-green 150D. Thickness: Considered thin — 0.2 mm. Texture: Brittle. Lenticels: Lightly prominent. Shape: Round. Number/sq. cm: 7-15, number increases towards apex. Color: from the White group 155B. Background: from the Yellow-green group 145A.

*Core*.—Position: Distant. Core Line Position: Median. Shape: Ovate. Length: Ranges from 25.0 mm to 29.6 mm with an average of 26.8 mm. Diameter: Ranges from 25.1 mm to 33.3 mm with an average of 29.9 mm.

*Cell*.—Tufted: No. Carpel shape: Obovate. Size: Length: Ranges from 17.0 mm to 22.5 mm. with an average of 19.1 mm. Width: Ranges from 11.0 mm to 12.6 mm with an average of 11.7 mm. Wall to Wall: Ranges from 3.7 mm to 5.2 mm with an average of 4.5 mm.

*Tube*.—Funnel shaped.

*Stamen position*.—Median.

*Axis*.—Axil and closed.

*Seed*.—Number: 1-2, mostly 2. Shape: 50% obtuse, 50% acute. Size: Length: Ranges from 7.8 mm to 9.5 mm with an average of 8.7 mm. Width: Ranges from 4.4 mm to 5.0 mm with an average of 4.8 mm. Depth: (wall to wall): Ranges from 2.3 mm to 3.1 mm with an average of 2.7 mm. Color: From the Grey-brown group 199A.

*Flesh*.—Very firm, juicy, sub-acid. Resists browning following cutting. Color: From the White group 155D.

*Aroma*.—Light apple like.

*Date of harvest maturity*.—Sep. 17, 2018.

*Maturity indices*.—Pressure: 20.2 pounds. Starch: 5.4 (Cornell Scale). Soluble Solids: 12.8 brix. pH: 3.57. Acid: 0.624 g/100 ml titratable acidity.

*Keeping quality*.—Very good, at least 5 months in common storage.

*Pollination*.—Most diploid apples of the same bloom season. Incompatibility alleles are not yet determined.

Use: Desert. Excellent eating quality that is snappy very firm, juicy, and sub-acid.

DNA typing: Like both parents ('Honeycrisp' and 'Cripps Pink'), 'WA 64' is heterozygous for the ACS1 gene and homozygous (2,2) for the ACO1 gene, both of which are involved in ethylene production, which in turn affects storage life.

Disease and insect resistance: 'WA 64' is considered to be susceptible to all insects and diseases found in the region of Central Washington although no major susceptibility issues have been noted. Fruit does not exhibit any physiological disorders on the tree nor during storage for the duration of normal storage lengths. 'WA 64' is free of all viruses recommended for testing by the National Clean Plant Network (NCPN).

The invention claimed is:

1. A new and distinct apple tree variety named 'WA 64' as herein shown and described.

* * * * *